US009194928B2

(12) United States Patent
Miyazaki

(10) Patent No.: US 9,194,928 B2
(45) Date of Patent: Nov. 24, 2015

(54) MAGNETIC RESONANCE IMAGING APPARATUS AND MAGNETIC RESONANCE IMAGING METHOD

(75) Inventor: Mitsue Miyazaki, Mount Prospect, IL (US)

(73) Assignees: KABUSHIKI KAISHA TOSHIBA, Tokyo (JP); TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 770 days.

(21) Appl. No.: 11/896,942

(22) Filed: Sep. 6, 2007

(65) Prior Publication Data
US 2008/0071166 A1 Mar. 20, 2008

(30) Foreign Application Priority Data

Sep. 6, 2006 (JP) ................ P2006-241575
Mar. 30, 2007 (JP) ................ P2007-092643

(51) Int. Cl.
*A61B 5/05* (2006.01)
*G01R 33/563* (2006.01)
(Continued)

(52) U.S. Cl.
CPC ........... *G01R 33/5635* (2013.01); *A61B 5/0263* (2013.01); *A61B 5/055* (2013.01); *G01R 33/3415* (2013.01); *G01R 33/546* (2013.01); *G01R 33/5601* (2013.01); *G01R 33/5605* (2013.01); *G01R 33/5607* (2013.01); *G01R 33/5673* (2013.01); *G01R 33/56341* (2013.01); *G01R 33/56383* (2013.01)

(58) Field of Classification Search
CPC ........ A61B 6/488; A61B 6/481; A61B 6/504; A61B 5/021; A61B 5/026

USPC ........... 600/410, 409, 407; 324/307, 306, 309
See application file for complete search history.

(56) References Cited

U.S. PATENT DOCUMENTS 5,204,627 A * 4/1993 Mistretta et al. ............... 324/309
5,291,891 A * 3/1994 Foo et al. ....................... 600/410
(Continued)

FOREIGN PATENT DOCUMENTS

JP 2000-005144 1/2000
JP 2002-010992 1/2002
(Continued)

OTHER PUBLICATIONS

Miyazaki et al., "Non-Contrast-Enhanced MR Angiography Using 3D ECG-Synchronized Half-Fourier Fast Spin Echo," Journal of Magnetic Resonance Imagining, 12:776-783 (2000).
(Continued)

*Primary Examiner* — Tse Chen
*Assistant Examiner* — Joel F Brutus
(74) *Attorney, Agent, or Firm* — Nixon & Vanderhye P.C.

(57) ABSTRACT

A magnetic resonance imaging apparatus includes an imaging condition setting unit, a data acquisition unit and an image data generating unit. The imaging condition setting unit sets respective imaging conditions corresponding to plural imaging regions. The respective imaging conditions include at least one non-contrast-enhanced imaging condition. The data acquisition unit acquires respective pieces of data corresponding to the plural imaging regions according to the respective imaging conditions. The image data generating unit generates image data based on the respective pieces of data corresponding to the plural imaging regions.

15 Claims, 6 Drawing Sheets

(51) Int. Cl.
*A61B 5/026* (2006.01)
*A61B 5/055* (2006.01)
*G01R 33/3415* (2006.01)
*G01R 33/54* (2006.01)
*G01R 33/56* (2006.01)
*G01R 33/567* (2006.01)

(56) References Cited

U.S. PATENT DOCUMENTS

| | | | |
|---|---|---|---|
| 5,320,099 A * | 6/1994 | Roberts et al. | 600/413 |
| 5,590,653 A * | 1/1997 | Aida et al. | 600/411 |
| 5,830,143 A | 11/1998 | Mistretta et al. | |
| 6,144,201 A | 11/2000 | Miyazaki | |
| 6,484,048 B1 * | 11/2002 | Hoshino et al. | 600/410 |
| 6,782,286 B2 | 8/2004 | Miyazaki | |
| 6,801,800 B2 | 10/2004 | Miyazaki et al. | |
| 6,900,635 B1 * | 5/2005 | Petropoulos et al. | 324/318 |
| 7,081,750 B1 * | 7/2006 | Zhang | 324/309 |
| 2002/0032376 A1 * | 3/2002 | Miyazaki et al. | 600/410 |
| 2004/0059213 A1 * | 3/2004 | Kassai et al. | 600/410 |
| 2005/0008206 A1 * | 1/2005 | Kawano | 382/128 |
| 2005/0228255 A1 * | 10/2005 | Saracen et al. | 600/407 |
| 2006/0058635 A1 * | 3/2006 | Lehtonen-Krause | 600/410 |
| 2008/0081987 A1 | 4/2008 | Miyazaki | |

FOREIGN PATENT DOCUMENTS

| | | |
|---|---|---|
| JP | 2003-135430 | 5/2003 |
| JP | 2003-334177 A | 11/2003 |
| JP | 2004-329614 | 11/2004 |
| JP | 2006-130116 | 5/2006 |
| WO | 2006/028015 A1 | 3/2006 |

OTHER PUBLICATIONS

Chinese Office Action dated Oct. 30, 2009 in CN2007101045851.
U.S. Appl. No. 11/896,941, filed Sep. 6, 2007, Miyazaki.
Japanese Office Action dated May 22, 2012 in JP 2007-092643.

* cited by examiner

| NON-CONTRAST MRA IMAGING CONDITION ||||||
|---|---|---|---|---|---|
| REGIONS || MORPHOLOGY | FUNCTION | ORDER | PI SCALE FACTOR (PE × SLICE) |
| HEAD || ◎3D TOF WITH MTC<br>○3D TOF WITHOUT MTC | ○ECG-PREP WITH<br>t-SLIP(CSF flow) | 1 | 4 × 2 |
| NECK || ◎3D TOF WITH WET<br>○3D TOF WITHOUT WET<br>○2D TOF | | 2 | 3 × 2 |
| CHEST | ARCH | ○SSFP<br>◎cine SSFP<br>○3D SSFP<br>○FBI | ○2D cine<br>○t-SLIP SSFP<br><br>○t-SLIP FBI | 3 | 3 × 2 |
| | PULMONARY | ○3D SSFP<br>○FBI | ○t-SLIP SSFP<br>○t-SLIP FBI | | 3 × 2 |
| | SUBCLAVIAN | ○SSFP<br>○FBI | | | 3 × 2 |
| AORTA || ○SSFP<br>◎FBI | | 4 | 3 × 2 |
| ABDOMEN | RENAL | ○SSFP<br>○FBI | ◎t-SLIP 3D SSFP<br>○t-SLIP FBI | 5 | 4 × 2 |
| | PORTAL VEIN | ○SSFP<br>○FBI | ○t-SLIP 3D SSFP<br>○t-SLIP FBI | | 4 × 2 |
| PERIPHERAL | ILIAC | ◎FS-FBI<br>(SPOILER −10, −5, 0, +5, ...)<br>DIASTOLE SPOILER  0<br>SYSTOIC SPOILER  −10 | | 6 | 3 × 2 |
| | THIGH | ◎FS-FBI<br>(SPOILER −10, −5, 0, +5, ...)<br>DIASTOLE SPOILER  0<br>SYSTOIC SPOILER  0 | | 7 | 3 × 2 |
| | CALF | ◎FS-FBI<br>(SPOILER −10, −5, 0, +5, ...)<br>DIASTOLE SPOILER  0<br>SYSTOIC SPOILER  +10 | | 8 | 3 × 2 |
| | FOOT | ◎FS-FBI<br>(SPOILER −10, −5, 0, +5, ...)<br>DIASTOLE SPOILER  0<br>SYSTOIC SPOILER  +30 | | 9 | 3 × 2 |
| | HAND | ◎FS-FBI<br>(SPOILER −10, −5, 0, +5, ...)<br>DIASTOLE SPOILER  0<br>SYSTOIC SPOILER  +20 | | | 3 × 2 |

IMAGE PROCESSING
AUTO SUBTRACTION ◎
AUTO MIP (3D)    ◎

FIG. 9

MAGNETIC RESONANCE IMAGING APPARATUS AND MAGNETIC RESONANCE IMAGING METHOD

RELATED APPLICATION

This application is related to copending application Ser. No. 11/896,941 filed Sep. 6, 2007.

BACKGROUND OF THE INVENTION

1. Field of the Invention

The present invention relates to an MRI (magnetic resonance imaging) apparatus and a magnetic resonance imaging method which excites nuclear spin of an object magnetically with an RF (radio frequency) signal having the L armor frequency and reconstructs an image based on NMR (nuclear magnetic resonance) signals generated due to the excitation, and more particularly, to a magnetic resonance imaging apparatus and a magnetic resonance imaging method, which can set imaging conditions for each of plural imaging regions and acquire data from the respective imaging regions according to the set imaging conditions.

2. Description of the Related Art

An MRI is an imaging method that excites an atomic nuclear spin of an object disposed in a static magnetic field by using an RF signal having a Larmor frequency and reconstructs the image on the basis of an NMR signal generated by the excitation.

In the field of magnetic resonance imaging, as a method of obtaining an image of a blood flow, MRA (magnetic resonance angiography) is known. MRI that does not use a contrast medium is referred to as a non-contrast-enhanced MRA. As non-contrast-enhanced MRA, an FBI (fresh blood imaging) method that performs an ECG (electro cardiogram) or peripheral pulse gating (PPG) synchronization to capture a pumping blood flow ejected from the heart is known, thereby satisfactorily representing a blood vessel (see, for example, Japanese Patent Application (Laid-Open) No. 2000-5144).

As non-contrast-enhanced MRA by the FBI method, an MRA image in which an artery and a vein are distinguished from each other is obtained by obtaining a difference between image data acquired by changing a delay time of ECG synchronization. Further, a flow-spoiled FBI method for suppressing an artery signal at systole by applying a spoiler pulse in the FBI method is known. According to the flow-spoiled FBI method, a difference between artery signals at diastole and systole of the cardiac cycle is imaged. In addition, an ECG-prep scan for determining an optimum delay time for ECG synchronization is known.

Further, in the FBI method, in order to extract blood flow having low flow velocity, a flow-dephasing method in which a gradient pulse (Gspoil) is applied in an RO (readout) direction, and a dephase pulse or a rephase pulse is applied as a gradient magnetic field pulse is known (see, for example, Japanese Patent Application (Laid-Open) No. 2002-200054, Japanese Patent Application (Laid-Open) No. 2003-135430 and U.S. Pat. No. 6,801,800). According to the flow-dephasing method, due to the dephase pulse or the rephase pulse, it is possible to increase relative signal difference between a signal value from blood flow having UM high velocity and a signal value from the blood flow having Hall low velocity. Therefore, it is possible to clearly distinguish an artery and a vein from each other on the basis of relative flow speed difference.

Furthermore, a technique for applying a t-SLIP (Time-SLIP: Time-Spatial Labeling Inversion Tagging Pulse) to selectively image or suppress only blood flowing into an imaging section is known (see, for example, Japanese Patent Application (Laid-Open) No. 2001-252263). In this t-SLIP method, a t-SLIP is applied with a constant delay time from an R wave of an ECG signal to label blood flowing into an imaging area. Consequently, signal intensity of blood that reaches an imaging section after a TI (inversion time) is enhanced.

Further, a technique to obtain dynamic state information of blood flow simply without a contrast medium and measuring an ECG-synchronization timing by the ECG-prep scan is known (see, for example, Japanese Patent Application (Laid-Open) No. 2004-329614). This technique uses an ECG-prep scan as an imaging scan. This means dynamic state information of blood flow can be obtained by subtraction processing to pieces of two-dimensional data acquired by plural acquisitions under an imaging scan, like an ECG-prep scan, while gradually changing a delay time from an R wave of an ECG signal.

Meanwhile, a receiver RF coil to receive an NMR signal may be used as an RF coil to transmit an RF signal. However, in many cases, a dedicated receiver RF coil according to an imaging region is used. For example, an array coil composed by aligning coil elements in a body axis direction is proposed as a coil for spine (see, for example, Japanese Patent Application (Laid-Open) No. H5-261081). In case of imaging an entire abdomen, multiple coil elements are arranged so as to encircle an object and NMR signals are received from the entire abdomen (see, for example, Japanese Patent Application (Laid-Open) No. 2003-334177).

However, since a coil element is necessary to be arranged with respect to every imaging region, there is a problem when the number of coil elements increases. In addition, a user needs to replace a set coil element to one suitable for the imaging region each time an object or an imaging region changes. For this reason, a user needs to prepare many dedicated coil elements suitable for imaging regions, and replacement of a coil element is a very onerous task for a user such as a doctor and an engineer in the field.

Therefore, a technique has been designed to provide a switching circuit and/or a synthetic circuit (matrix) regarding multiple coil elements lined up in an X-axis direction perpendicular to a body axis of an object to enable modal selection of combinations of coil elements used for receiving (see, for example, Japanese Patent Application (Laid-Open) No. 2003-334177).

The conventional blood flow imaging is performed per section by moving a receiver RF coil specialized for an imaging region in contrast to imaging an organ and an internal organ. That is, a user moves a receiver RF coil to a position suitable for imaging blood flow in a section to be a next target after imaging blood flow with regarding to a certain section. Then, after a position of the RF coil is determined, blood flow in a corresponding section is imaged.

Imaging blood flow can be performed over multiple imaging regions where dedicated receiver RF coils mutually differ. In this case, a receiver RF coil needs to be replaced each time an imaging region changes. Especially in imaging blood flow throughout an entire body, an RF coil needs to be replaced frequently.

Furthermore, when an imaging sequence suitable for imaging blood flow varies every imaging region, a user needs to reset an imaging sequence each time an imaging region changes.

Thus, in imaging widespread blood flow, in addition to an onerous task such as selection and placement of a receiver RF coil, a user may encounter a troublesome operation such as resetting an imaging sequence. These are common problems in acquiring a widespread image as well as imaging blood flow.

SUMMARY

The present exemplary embodiment has been made in light of such conventional situations, and it is an object of the present invention to provide a magnetic resonance imaging apparatus and a magnetic resonance imaging method which make it possible to acquire an image of a large area as typified by a blood flow image with easier operations.

The present exemplary embodiment provides a magnetic resonance imaging apparatus comprising: an imaging condition setting unit configured to set respective imaging conditions corresponding to plural imaging regions, the respective imaging conditions including at least one non-contrast-enhanced imaging condition; a data acquisition unit configured to acquire respective pieces of data corresponding to the plural imaging regions according to the respective imaging conditions; and an image data generating unit configured to generate image data based on the respective pieces of data corresponding to the plural imaging regions, in an aspect to achieve the object.

The present exemplary embodiment also provides a magnetic resonance imaging method comprising steps of: setting respective imaging conditions corresponding to plural imaging regions, the respective imaging conditions including at least one non-contrast-enhanced imaging condition; acquiring respective pieces of data corresponding to the plural imaging regions according to the respective imaging conditions; and generating image data based on the respective pieces of data corresponding to the plural imaging regions, in an aspect to achieve the object.

The magnetic resonance imaging apparatus and the magnetic resonance imaging method as described above make it possible to acquire an image of a large area as typified by a blood flow image with easier operations.

BRIEF DESCRIPTION OF THE DRAWINGS

In the accompanying drawings:

FIG. 9 is a diagram showing an example of setting window for imaging conditions displayed as a user interface on the monitor shown in FIG. 1.

DESCRIPTION OF THE PREFERRED EMBODIMENTS

A magnetic resonance imaging apparatus and a magnetic resonance imaging method according to exemplary embodiments of the present invention will be described with reference to the accompanying drawings.

Figure 1:
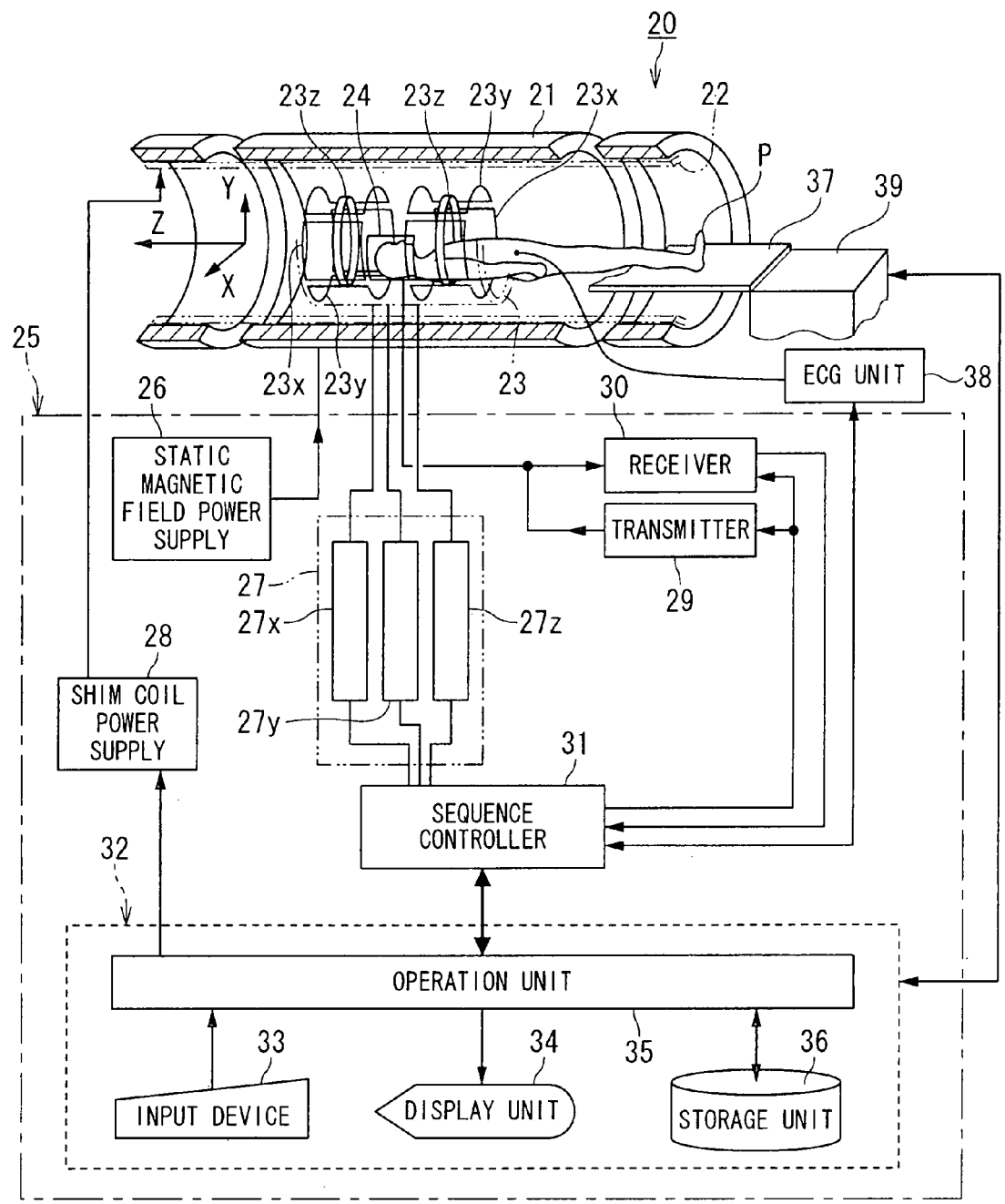
FIG. 1 is a block diagram showing a magnetic resonance imaging apparatus according to an exemplary embodiment of the present invention.

FIG. 1 is a block diagram showing a magnetic resonance imaging apparatus according to an exemplary embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and a RF coil 24. The static field magnet 21, the shim coil 22, the gradient coil 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27$x$, a Y-axis gradient power supply 27$y$ and a Z-axis gradient power supply 27$z$. The computer 32 includes an input device 33, a monitor 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23$x$, a Y-axis gradient coil 23$y$ and a Z-axis gradient coil 23$z$. Each of the X-axis gradient coil 23$x$, the Y-axis gradient coil 23$y$ and the Z-axis gradient coil 23$z$ which is cylinder-shaped is arranged inside the static field magnet 21. The gradient coil 23 has also a bed 37 in the area formed inside it which is an imaging area. The bed 37 supports an object P. Around the bed 37 or the object P, the RF coil 24 may be arranged instead of being built in the gantry.

The gradient coil 23 communicates with the gradient power supply 27. The X-axis gradient coil 23$x$, the Y-axis gradient coil 23$y$ and the Z-axis gradient coil 23$z$ of the gradient coil 23 communicate with the X-axis gradient power supply 27$x$, the Y-axis gradient power supply 27$y$ and the Z-axis gradient power supply 27$z$ of the gradient power supply 27 respectively.

The X-axis gradient power supply 27$x$, the Y-axis gradient power supply 27$y$ and the Z-axis gradient power supply 27$z$ supply currents to the X-axis gradient coil 23$x$, the Y-axis gradient coil 23y and the Z-axis gradient coil 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit an RF signal given from the transmitter 29 to the object P and receive an NMR signal generated due to a nuclear spin inside the object P which is excited by the RF signal to give to the receiver 30.

Figure 2:
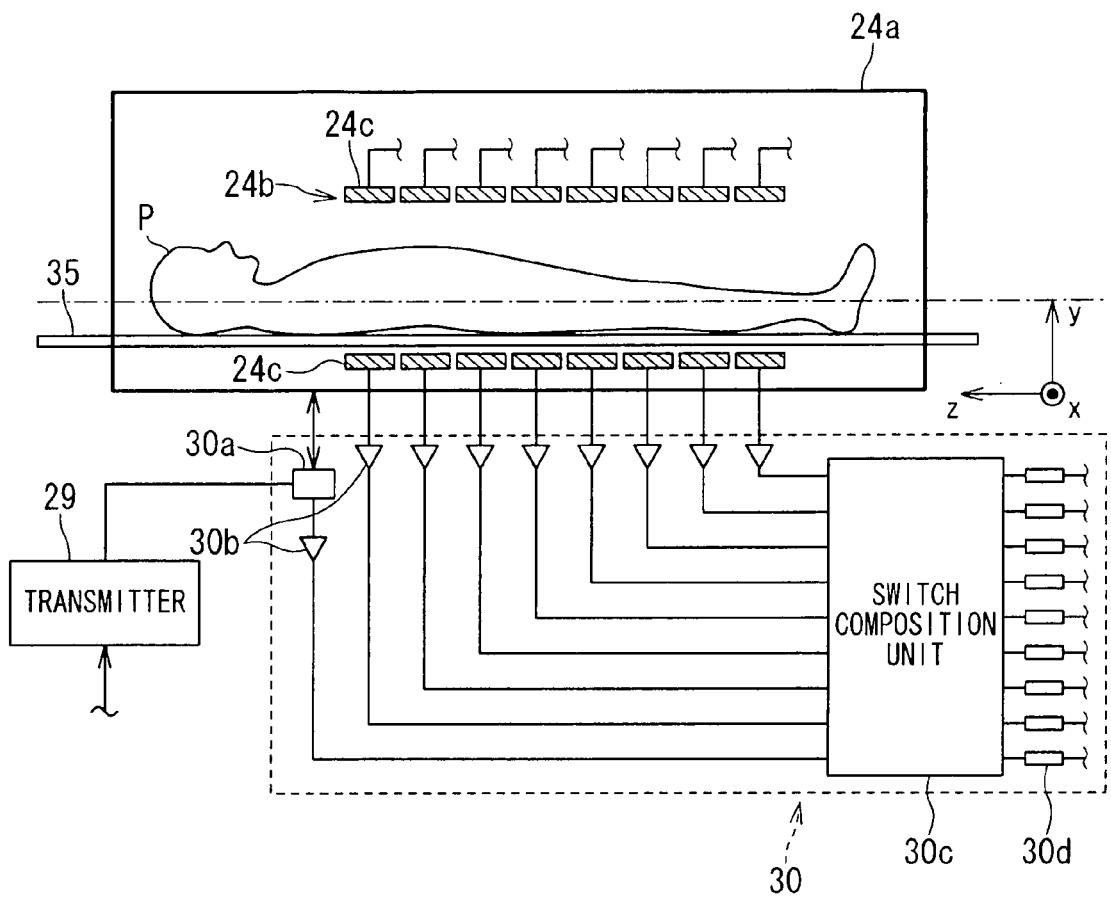
FIG. 2 is a diagram showing an example of detail structure of the RF coil shown in FIG. 1.
Figure 3:
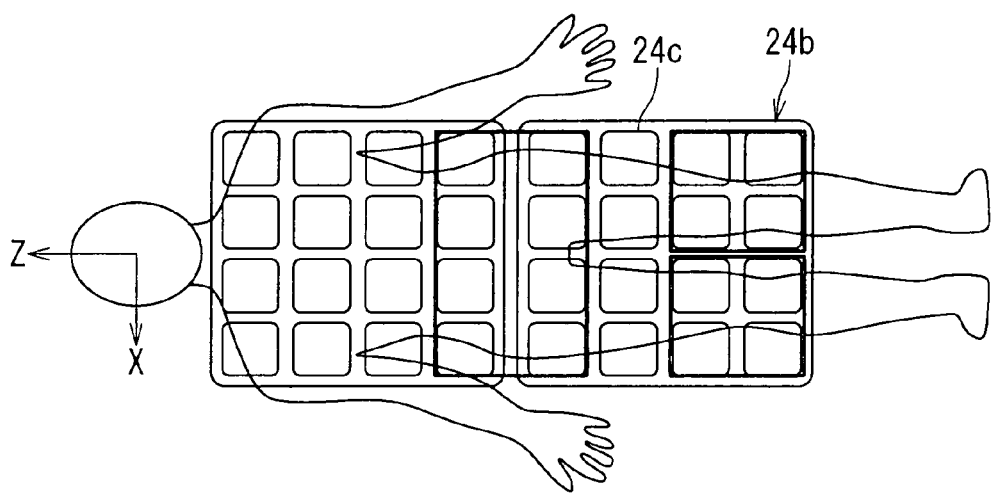
FIG. 3 is a diagram showing an example arrangement of the coil elements set on the body surface side of the object shown in FIG. 2.
Figure 4:
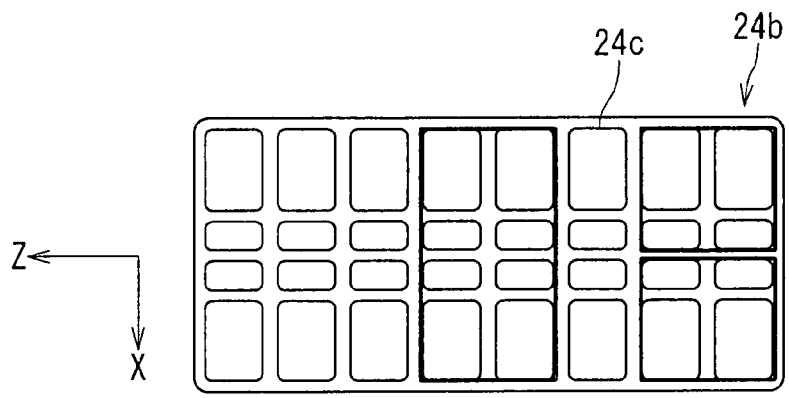
FIG. 4 is a diagram showing an example arrangement of the coil elements set on the back surface side of the object shown in FIG. 2.

FIG. 2 is a diagram showing an example of detail structure of the RF coil 24 shown in FIG. 1. FIG. 3 is a diagram showing an example arrangement of the coil elements 24c set on the body surface side of the object P shown in FIG. 2. FIG. 4 is a diagram showing an example arrangement of the coil elements 24c set on the back surface side of the object P shown in FIG. 2.

As shown in FIG. 2, the RF coil 24 includes a cylindrical WB (whole-body) coil 24a, and a phased array coil 24b. The phased array coil 24b includes a plurality of coil elements 24c, and a plurality of the coil elements 24c is arranged on each of the body surface side and the back surface side of the object P.

For example, as shown in FIG. 3, on the body surface side of the object P, four rows of coil elements 24c are provided in the x-direction and eight columns of them in the z-direction, that is, a total of thirty two coil elements 24c are arranged so as to cover a wide-ranging imaging area. Likewise, as shown in FIG. 4, on the back surface side of the object, four rows of coil elements 24c are provided in the x-direction and eight columns of them in the z-direction, that is, a total of thirty two coil elements 24c are arranged so as to cover a wide-ranging imaging area. On the back surface side, coil elements 24 with a smaller size than that of the other coil elements 24c are arranged in the vicinity of the body axis from the viewpoint of sensitivity improvement, considering for the presence of the backbone of the object P.

On the other hand, the receiver 30 includes a duplexer 30a, amplifiers 30b, a switch composition unit 30c, and reception circuits 30d. The duplexer 30a is connected to the transmitter 29, the WB coil 24a, and the amplifier 30b for the WB coil 24a. The amplifiers 30b are provided by the total number of the coil elements 24c and the WB coil 24a, and each connected to a respective one of the coil elements 24c and the WB coil 24a. The switch composition unit 30c consists of a single piece or a plurality of pieces. The input side of the switch composition unit 30c is connected to the plurality of coil element units 24c or the WB coil 24a through the plurality of amplifiers 30b. The reception circuits 30d are provided by a desired number such as to be smaller than or equal to the total number of the coil elements 24c and the WB coil 24a, and disposed on the output side of the switch composition unit 30c.

The WB coil 24a can be used as a coil for the transmission of radio frequency signals. As a coil for the reception of NMR signals, each of the coil elements 24c can be used. Furthermore, the WB coil 24a can also be used for a receiving coil.

Therefore, the duplexer 30a is configured so as to provide the WB coil 24a with radio frequency signals for transmission, outputted from the transmitter 29, while providing the switch composition unit 30c with NMR signals received in the WB coil 24a via the amplifiers 30b in the receiver 30. An NMR signal received in each of the coil elements 24c is outputted to the switch composition unit 30c via a respective one of the amplifiers 30b.

The switch composition unit 30c is configured so as to perform composition processing and switching with respect to NMR signals received from the coil elements 24c or the WB coil 24a and to output them to the corresponding reception circuits 30d. In other words, the switch composition unit 30c is configured so that, in conformance with the number of the reception circuits 30d, the composition processing and switching with respect to NMR signals received from the coil elements 24c or the WB coil 24a are performed in the switch composition unit 30c, and that NMR signals can be received from various imaging areas by forming sensibility distributions in response to the imaging areas, using a plurality of desired coil elements 24c.

However, NMR signals may be received by WB coil 24a alone without providing the coil elements 24c. Also, NMR signals received in the coil elements 24c or the WB coil 24a may be directly outputted to the reception circuits 30d without providing the switch composition unit 30c. Furthermore, more coil elements 24c may be extensively arranged.

Figure 5:
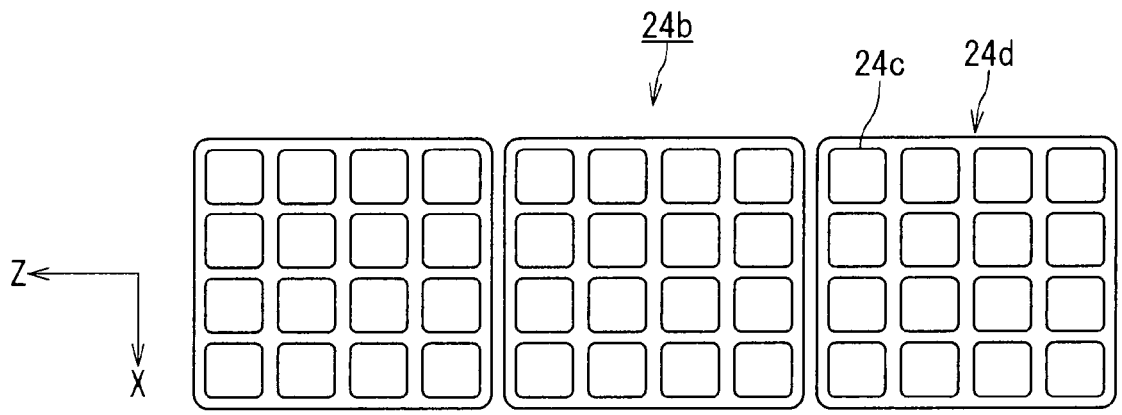
FIG. 5 is a diagram showing another example arrangement of the coil elements set on the body surface side of the object shown in FIG. 2.
Figure 6:
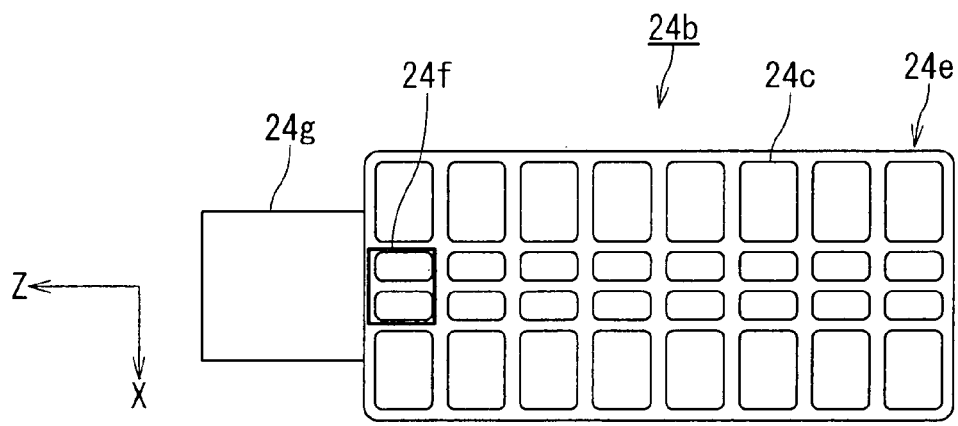
FIG. 6 is a diagram showing another example arrangement of the coil elements set on the back surface side of the object shown in FIG. 2.

FIG. 5 is a diagram showing another example arrangement of the coil elements 24c set on the body surface side of the object P shown in FIG. 2. FIG. 6 is a diagram showing another example arrangement of the coil elements 24c set on the back surface side of the object P shown in FIG. 2.

As shown in FIGS. 5 and 6, further more coil elements 24c may be arranged around the object P. In an example shown in FIG. 5, three coils 24d each composed of sixteen elements constituted of four columns of coil elements 24c in the x-direction and four rows of coil elements 24c in the z-direction are arranged in the z-direction, that is, a total of forty eight elements of coil elements 24c are arranged on the body surface side of the object P. On the other hand, in an example shown in FIG. 6, a coil 24e composed of thirty two elements constituted of four columns of coil elements 24c in the x-direction and eight rows of coil elements 24c in the z-direction are arranged on the backbone side of the object P; a coil 24f having coil elements 24c composed of two elements (not shown) are arranged in the vicinity of jaws; and further a coil 24g having coil elements 24c composed of twelve elements (not shown) are arranged under the head, that is, a total of forty six elements of coil elements 24c are arranged on the back surface side of the object P. Arranging the coil elements 24c on the body surface side and back surface side of the object P as shown in FIGS. 5 and 6 results in that a total of ninety four elements of coil elements 24c are arranged around the object P. Each of the coil elements 24c is connected to a respective exclusive one of the amplifiers 30b via a coil port (not shown).

Arranging a multitude of coil elements 24c around the object P makes it possible to form a phased array coil 24b for the whole-body, capable of receiving data from a plurality of imaging areas without moving the positions of the coils or that of the object P. Although the WB coil 24a can also receive data from a plurality of imaging areas without moving the positions of the coils or that of the object P, the use of the phased array coil 24b as a receiving coil allows data to be received with sensitivities more suitable for the imaging areas and with a better SNR (signal-to-noise ratio).

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex number data obtained through the detection of an NMR signal and A/D conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG (electro cardiogram) unit 38 for acquiring an ECG signal of the object P is provided with the magnetic resonance imaging apparatus 20. The ECG signal acquired by the ECG unit 38 is outputted to the computer 32 through the sequence controller 31.

Furthermore, the bed 37 is provided with a table drive unit 39. The table drive unit 39 is connected with the computer 32 so as to move the table of the bed 37 under the control by the computer 32 for imaging with moving table method or stepping table method. The moving table method is a technique for obtaining a large FOV (field of view) in a moving direction by continuously moving the table of the bed 37 during imaging. The stepping table method is a technique for three-dimensional imaging at every station by stepping the table of the bed 37. These techniques are used in case of imaging a large area which is unable to be imaged at a time such as whole body imaging. The images acquired with moving the bed 37 may be combined mutually by compound processing in the computer 32.

The computer 32 gets various functions by the operation unit 35 executing some programs stored in the storage unit 36 of the computer 32. The computer 32 may include some specific circuits instead of using some of the programs.

Figure 7:
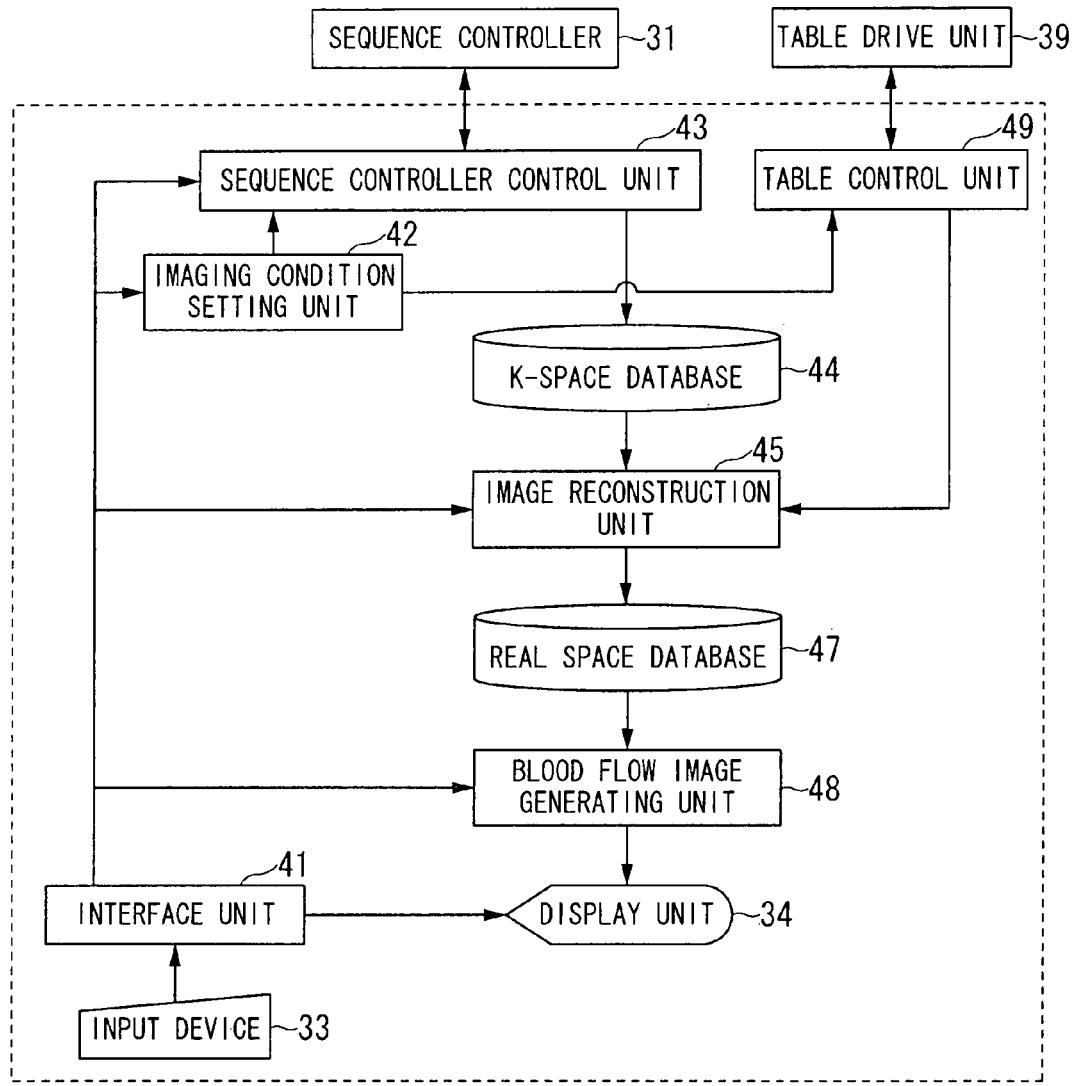
FIG. 7 is a functional block diagram of the computer shown in FIG. 1.

FIG. 7 is a functional block diagram of the computer 32 shown in FIG. 1.

The computer 32 functions as an interface unit 41, an imaging condition setting unit 42, a sequence controller control unit 43, a k-space data database 44, an image reconstruction unit 45, a real space data database 47, a blood flow image generating unit 48 and a table control unit 49 by program.

The interface unit 41 has a function to display a setting window for setting and inputting various information on the display unit 34 by the GUI (Graphical User Interface) technology, receive instruction information from the input device 33 and provide it to a corresponding element. Set information includes information such as an imaging condition and an image processing method.

Especially through the setting window of an imaging condition, imaging conditions with regard to imaging over multiple imaging regions such as a head, a chest, an abdomen and a lower limb can be set collectively. Therefore, pieces of data can be acquired from each imaging region without resetting an imaging condition over multiple imaging regions. Since the WB coil 24a and/or the phased array coil 24b for an entire body as described above are used for data acquisition, positions of a coil and an object P do not need to be changed. This makes it possible to acquire data sequentially and automatically from multiple imaging regions.

A blood flow image is cited as a major target image for imaging over multiple imaging regions. Especially multiple imaging regions may be a target of non-contrast-enhanced MRA without using contrast medium. Therefore, if an imaging condition for non-contrast-enhanced MRA is set for multiple imaging regions, vessels throughout an entire body can be imaged sequentially without administering contrast medium. Here, description will be given as in case where imaging conditions for non-contrast-enhanced MRA are set.

A method for selecting a desired one from possible pulse sequences for imaging according to every imaging region in advance is cited as a concrete method for setting imaging conditions. In addition, since image processing way of data acquired depending on an imaging condition may change, an image processing way also can be set through a setting window before acquiring data. For example, in case of acquiring three-dimensional data, instruction of whether to perform projection processing such as MIP (maximum intensity projection) processing automatically can be provided through the setting window before data acquisition, and in case of generating an MRA image with arteriovenous separation from pieces of image data in a diastole and a systole of a cardiac cycle, instruction of whether to perform subtraction processing automatically can be provided through the setting window before data acquisition. That is to say, automatically performing of image processing such as projection processing and subtraction processing as post-processing to image data can be instructed before data acquisition in advance.

With regard to subtraction processing, it is possible to instruct weighted subtraction processing as well as simple subtraction processing. In other words, subtraction processing can be performed with multiplying arbitrary coefficients by processing targets respectively. For example, when coefficients for pieces of image data I1 and I2 serving as targets of weighted subtraction processing are 0.7 and 1.0 respectively, weighted subtraction processing is presented by 0.7I1-1.0I2.

In addition, imaging under moving table method or stepping-table method with movement of the table top of the bed 37 can be instructed from the input device 33 as an imaging condition. In this case, positional information of the table top is associated with a pulse sequence used for imaging. That is, a pulse sequence can be set depending-on a position of the table top. In case of acquiring respective data from multiple imaging regions by the stepping-table method, the table top of the bed 37 for setting an object P is moved each time data acquisition at a single imaging region is completed.

When an imaging condition is instructed, it is provided from the interface unit 41 to the imaging condition setting unit 42 and the image reconstruction unit 45. When an image processing way relating to generating a blood flow image is instructed, it is provided from the interface unit 41 to the blood flow image generating unit 48. When an instruction to start a scan is provided from the input device 33, the instruction to start data acquisition is provided from the interface unit 41 to the sequence controller control unit 43.

The imaging condition setting unit 42 has a function to provide the set imaging condition such as a pulse sequence to the sequence controller control unit 43 according to the instruction of pulse sequence obtained from the input device 33 through the interface unit 41. When imaging by moving table method or stepping-table method with movement of the table top of the bed 37 is instructed from the input device 33 through the interface unit 41, the imaging condition setting unit 42 is configured to provide positional information of the table top of the bed 37 to the table control unit 49.

The sequence controller control unit 43 has a function for controlling and driving the sequence controller 31 by giving imaging condition information indicating imaging conditions including a pulse sequence acquired from the imaging condition setting unit 42 to the sequence controller 31 according to a scan start instruction obtained from the input device 33 via the interface unit 41 or another element. Further, the sequence controller control unit 43 has a function for receiving raw data which is k-space (Fourier space) data from the sequence controller 31 and arranging the raw data to k-space formed in the k-space database 44.

The k-space database 44 stores k-space data given from the sequence controller control unit 43.

The image reconstruction unit 45 has a function for capturing k-space data from the k-space database 44, performing image reconstruction processing, such as Fourier transform processing, corresponding to a pulse sequence acquired from the input device 33 via the interface unit 41 to generate image data from the k-space data, and writing the generated image data to the real space data database 47. When imaging by moving table method or stepping-table method with movement of the table top of the bed 37 is instructed from the input device 33 through the interface unit 41 and multiple images respectively acquired at different table top positions are instructed to display as a single image, the image reconstruction unit 45 is configured to perform compound processing for combining image data, generated by image reconstruction processing, based on the positional information of the table top obtained from the table control unit 49.

The blood flow image generating unit 48 has a function to obtain image data stored in the real space database 47, generate blood flow image data according to the instruction of an image processing way from the interface unit 41 and display the generated blood flow image data on the display unit 34. The blood flow image generating unit 48, for example, is configured to generate an MRA image with arteriovenous separation by performing subtraction processing between pieces of image data acquired in a diastole and a systole of a cardiac cycle respectively, and generate a projection image for displaying by performing projection processing to three-dimensional blood flow image data.

The table control unit 49 is configured to control the table drive unit 39 so that the table top of the bed 37 moves to an appropriate position in conformity with performance of a pulse sequence in case of receiving an instruction of imaging by the moving table method or the stepping-table method from the imaging condition setting unit 42, and to provide the positional information of the table top of the bed 37 to the image reconstruction unit 45.

Next, the operation and action of a magnetic resonance imaging apparatus 20 will be described.

Figure 8:
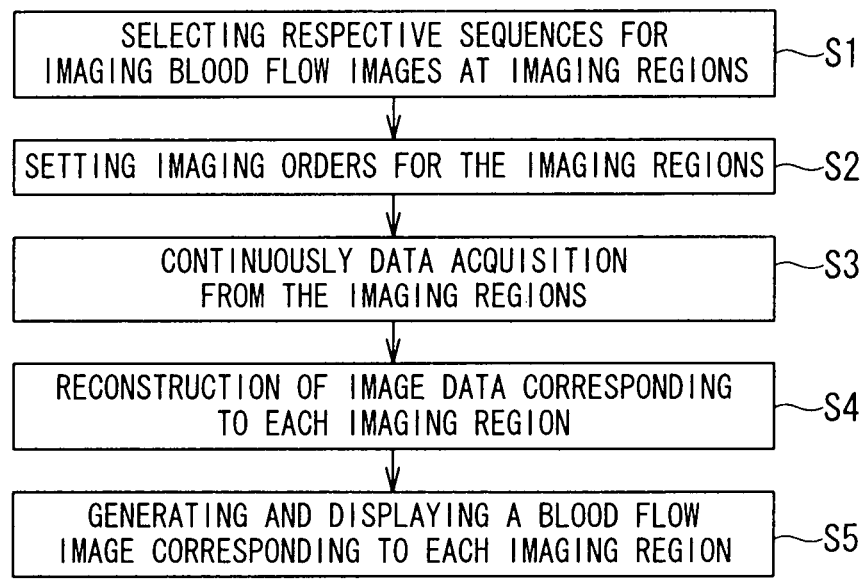
FIG. 8 is a flowchart showing a flow for imaging a non-contrast-enhanced MRA image of whole-body of the object with the magnetic resonance imaging apparatus shown in FIG. 1.

FIG. 8 is a flowchart showing a flow for imaging a non-contrast-enhanced MRA image of whole-body of the object P with the magnetic resonance imaging apparatus 20 shown in FIG. 1. The symbols including S with a number in FIG. 8 indicate each step of the flowchart.

In the step S1, respective pulse sequences corresponding to imaging regions are selected as imaging conditions for acquiring a non-contrast-enhanced MRA image. For this purpose, window information is provided from the interface unit 41 to the display unit 34, and a setting window for setting an imaging condition and an image processing way is displayed on the display unit 34.

FIG. 9 is a diagram showing an example of setting window for imaging conditions displayed as a user interface on the monitor 34 shown in FIG. 1.

For example, in the setting window as shown in FIG. 9, a different pulse sequence can be selected as an imaging condition to every imaging region (REGIONS). Each pulse sequence can be selected by checking the cell displayed near the pulse sequence to be selected by operation of the input device 33 in the setting window shown in FIG. 9. However, it is acceptable to configure a pull down menu for selecting a pulse sequence.

As an example shown in FIG. 9, HEAD, NECK, CHEST, AORTA, ABDOMEN and PERIPHERAL are displayed as imaging regions. CHEST is categorized into ARCH, PULMONARY and SUBCLAVIAN. ABDOMEN is categorized into RENAL and PORTAL VEIN. PERIPHERAL is categorized into ILIAC, THIGH, CALF, FOOT and HAND.

Pulse sequences selectable for imaging blood flow morphology and pulse sequences selectable for performing function MRA at respective imaging portions are displayed.

A 3D (three-dimensional) TOF (time of flight) sequence with application of MTC (magnetization transfer contrast) pulse can be cited as a pulse sequence used for imaging blood flow morphology of a head. A TOF sequence uses blood flow that flows into an imaging area to decrease a signal from a stationary tissue by excitation in a TR (repetition time) shorter than a longitudinal relaxation time (T1) of tissue, and also obtains a signal with high intensity from a blood flow by flow-in effect. An MTC pulse is a pulse to contrast a site with a lot of chemical alteration and a site with less chemical alteration of polymer and the free water by using magnetization transfer that disturbs an equilibrium state between hydrogen and free water detected as an MR signal by means of excitation of hydrogen around a protein with restricted movement, and then transfers magnetization of water with restricted movement to the free water.

Pulse sequences used for functional MRA of a head includes an ECG-prep sequence with an application of t-SLIP to image a CSF (cerebrospinal fluid) flow.

An ECG-prep sequence is a sequence for a pre-scan performed in advance of an imaging scan. An ECG-prep sequence acquires data repeatedly with changing a delay time from an R wave of an ECG signal. When performing a scan according to an ECG-prep sequence, pieces of image data corresponding to mutually different delay times are generated. Then, an appropriate delay time to be set as an imaging condition for an imaging scan is determined by reference to pieces of image data corresponding to the respective delay times.

The example in FIG. 9 shows selectable pulse sequences for functional MRA of a head and may show selectable pulse sequences for functional MRA of another portion. A delay time (time phase) determined by performing an ECG-prep sequence at a certain portion can be used as an imaging condition for an imaging scan at another portion. Therefore, even when multiple imaging portions are target for imaging, it may be enough to perform an ECG-prep sequence once at one portion.

For example, a delay time can be common to imaging of a head and a chest. Especially, when an FBI sequence is selected as an imaging condition for a chest as referred to hereinafter, it is important to control a timing of application of an IR (inversion recovery) pulse with a high degree of accuracy. An imaging condition for a chest has more constraint conditions than that for another portion. For this reason, an appropriate delay time for a chest can be set by performing an ECG-prep sequence for the chest and this set delay time for the chest can be used as a delay time for an FBI sequence for a lower limb.

A t-SLIT is applied after a certain delay time from an R wave of an ECG signal to selectively depict or suppress only blood flowing into an imaging section. A t-SLIT consists of a region non-selective inversion pulse and a region selective inversion pulse. The region non-selective inversion pulse can switch on/off. The region selective inversion pulse can be set arbitrarily independent of an imaging section. When blood flowing into an imaging area is labeled by a region selective inversion pulse, a signal intensity of a portion where the blood reached after a TI increases. When turning a region non-selective inversion pulse off, a signal intensity of a portion where the blood reached after a TI decreases. Therefore, a direction and/or a distance of blood movement can be figured out.

Imaging conditions for PI (parallel imaging) for acquiring data by multiple coil elements 24c can be set with regard to respective imaging portions. The PI receives echo data with multiple coil elements 24c and reduces the number of phase encodes to the number obtained by multiplying the reciprocal of the number of the coil elements 24c by the number of phase encodes necessary for image reconstruction, by skipping at least one phase encode.

When PI is performed, necessary information for PI including the number of coil elements 24c used for acquiring echo data and information that relates each coil element 24c with a corresponding imaging portion is set as imaging conditions. The number of coil elements 24c used for acquiring echo data is set as a speed scale (speeding-up rate). The speed scale can be set in a slice direction and a PE (phase encode) direction.

A speed scale for PI can be set arbitrarily to each imaging portion. In an example shown in FIG. 9, a speed scale in a PE direction for PI of a head is set to 4 and a speed scale in a slice direction is set to 2.

A speed scale for PI can be determined depending on a required SNR (signal to noise ratio) and/or a required CNR (contrast to noise ratio) of a blood vessel. For example, since imaging by an FBI sequence can generate a blood flow image having a better CNR of a blood vessel than another imaging method, a speed scale for PI can be set to a larger value than that of another imaging method. This means high-speed imaging can be performed with more coil elements 24c.

Further, a speed scale for PI can be also determined according to the number of the coil elements 24c located around respective imaging portions and/or sensitivity distributions formed by compound processing to and/or switching NMR signals outputted from coil elements 24c. For example, a speed scale for PI in an abdomen can be set to a larger value than that in a lower limb.

Though selection of a pulse sequence and setting a speed scale for PI can be performed as described above, it is also possible to combine these imaging conditions with other imaging conditions set by a conventional method for setting an imaging condition for non-entire body imaging. For example, for imaging a head, besides a TOF sequence, a DWI (diffusion weighted image) sequence or a FLAIR (fluid attenuated inversion recovery) sequence can be selected. A DWI sequence is a sequence to acquire an image with enhancing diffusion effect by applying an MPG (motion probing gradient) pulse. A FLAIR sequence is a sequence to suppress a water signal from CSF and the like showing a long T1 value by applying an inversion pulse of which TI=approximately 1500-2500 ms as a pre-pulse and to image an area showing a high signal intensity such as an infarction portion with clear contrast.

Meanwhile, a 2D TOF sequence or a 3D TOF sequence can be selected as an imaging condition for a neck portion. When a 3D TOF sequence is selected, whether to use WET (water excitation technique) can be instructed. WET includes a method for applying a binomial pulse to suppress a signal from a fat area and emphasize a signal from a water area. For this reason, when application of WET is instructed, a 3D TOF sequence with application of a binomial pulse is set as an imaging condition, for example.

An SSFP (steady state free precession) sequence and an FBI sequence are displayed on the setting window as selectable sequences for a head, an aorta, an abdomen and a lower limb. An SSFP sequence is a sequence to image with aligning phases of transverse magnetization at each repeated excitation and can acquire data independent of a direction of a blood flow.

An FBI sequence is a sequence to depict blood vessels clearly by acquiring a high-velocity blood flow pumped from a heart with an ECG synchronization. Specifically, by an FBI sequence, an MRA image with arteriovenous separation can be obtained by calculating subtraction between pieces of image data acquired in a diastole and a systole of a cardiac cycle with changing a delay time for an ECG synchronization. An FS (Flow-Spoiled)-FBI sequence is an FBI sequence with applying a spoiler pulse. When using an FS-FBI sequence, an imaging condition under Flow-dephasing method for applying a spoiler pulse in an RO (readout) direction can be set. An application of a spoiler pulse can increase a relative signal difference between a signal value from a high-velocity blood flow and a signal value of a low-velocity blood flow and perform clear arteriovenous separation from the relative signal difference. This allows depicting a low-velocity blood flow.

Especially in a lower limb, an intensity of a Spoiler pulse (Flow-dephasing value) can be set according to each imaging portion individually in a diastole and a systole. FIG. 9 shows an example of making it possible to set an intensity of a Spoiler pulse from −10 at intervals of 5.

In addition to this, a pulse sequence such as a phase contrast sequence according to phase contrast method can be cited as a pulse sequence for non-contrast-enhanced MRA. A phase contrast sequence is a sequence to perform an imaging method for depicting a blood flow with a target flow velocity using phase shift effect that phase of spins moving in a gradient magnetic field direction changes.

Then in step S2, an imaging order of imaging portions is set. An imaging order can be set after setting an imaging condition for a certain portion as well as after setting imaging conditions corresponding to the whole imaging portions. In an example of FIG. 9, the setting window is configured so that an imaging order can be inputted as numeric values. A user can specify an imaging order to each selected pulse sequence through operation of the input device 33.

By setting an imaging order, imaging over multiple imaging portions can be performed automatically and sequentially. For example, imaging conditions specified by multiple pulse sequences for non-contrast-enhanced MRA of an object P throughout body can be set.

In an example shown in FIG. 9, imaging conditions for non-contrast-enhanced MRA throughout the body are set so as to image sequentially in the order of the following, imaging a head by a 3D TOF WITH MTC sequence, imaging a neck by a 3D TOF WITH WET sequence, imaging a chest by a cine SSFP sequence, imaging an aorta by an FBI sequence, imaging a renal by a t-slip 3D SSFP sequence, imaging an iliac artery by an FS-FBI sequence with a spoiler pulse having an intensity of −10, imaging a thigh by an FS-FBI sequence with a spoiler pulse having an intensity of 0, imaging a calf by an FS-FBI sequence with a spoiler pulse having an intensity of +10 and imaging a foot by an FS-FBI sequence with a spoiler pulse having an intensity of +30.

In addition to an imaging condition and an imaging order, setting for automatically image processing can be performed through a setting window. In an example shown in FIG. 9, it can be set whether to automatically perform subtraction processing executed for obtaining an MRA image with arteriovenous separation to pieces of data acquired in a diastole and a systole with an FS-FBI sequence and to automatically perform MIP processing executed to generate an image for displaying when three-dimensional image data is generated. Meanwhile, whether to automatically perform subtraction processing and MIP processing may be set with regard to each imaging portion. Further, processing necessary to generate a blood flow image other than subtraction processing and MIP processing may be set through a setting window. By this means, a flow from data acquisition to image processing can be set by the operation of the input device 33 throughout the interface unit 41.

When pulse sequences are selected and an imaging order is set, the selected pulse sequences associates with geometric positional information of the corresponding imaging portions respectively, which is provided together with imaging order information indicating an imaging order from the interface unit 41 to the imaging condition setting unit 42. When automatic subtraction processing and/or automatic MIP processing are set, instructions of the automatic subtraction processing and/or the automatic MIP processing are provided from the interface unit 41 to the blood flow image generating unit 48.

In addition, when imaging by moving table method or stepping-table method is required due to positional relation between imaging portions and the coil elements 24c, instruction to image by the moving table method or the stepping-table method is automatically provided from the interface unit 41 to the imaging condition setting unit 42 and the image reconstruction unit 45. Alternatively, the instruction to image by the moving table method and the stepping-table method may be provided manually through operation of the input device 33 to the imaging condition setting unit 42 and the image reconstruction unit 45.

Then in step S3, when instruction to start to acquire data is provided through the interface unit 41 from the input device 33 to the sequence controller control unit 43, data acquisition starts. Specifically, the sequence controller control unit 43 sequentially provides the pulse sequences corresponding to the respective imaging portions acquired from the imaging condition setting unit 42 to the sequence controller 31 in accordance with the imaging order. The sequence controller 31 generates a gradient magnetic field in the imaging area where the object P is set by driving the gradient power supply 27, the transmitter 29 and the receiver 30 according to the pulse sequences received from the sequence controller control unit 43 and also generates a radio frequency signal from the RF coil 24.

Accordingly, an NMR signal generated by the nuclear magnetic resonance in the object P is received by the RF coil 24 and provided to the receiver 30. The receiver 30 performs the necessary signal processing to the NMR signal received from the RF coil 24, and then generates raw data that is an NMR signal of digital data by A/D conversion. The receiver 30 provides the generated raw data to the sequence controller 31. The sequence controller 31 provides the raw data to the sequence controller control unit 43 and the sequence controller control unit 43 arranges the raw data as K-space data in K-space formed in the K-space database 44.

The series of data acquisition as described above is performed according to the corresponding pulse sequences to the respective imaging portions in the imaging order. Especially when an instruction of imaging by the moving table method or the stepping-table method is provided from the interface unit 41 to the imaging condition setting unit 42, positional information of the table top of the bed 37 is provided from the imaging condition setting unit 42 to the table control unit 49.

Then, the table control unit 49 controls the table drive unit 39 so that the table top of the bed 37 moves to appropriate positions in accordance with execution of the pulse sequences. Further, the table control unit 49 provides the positional information of the bed 37 at respective data acquisitions to the image reconstruction unit 45. This allows acquisition of K-space data with moving the table top of the bed 37. Consequently, pieces of K-space data from respective imaging portions are stored in the K-space database 44.

Then in step S4, the image reconstruction unit 45 retrieves the K-space data from the K-space database 44 and generates the image data from the K-space data by performing, to the K-space data, image reconstruction processing such as Fourier transformation processing corresponding to the pulse sequences obtained through the interface unit 41 from the input device 33.

When multiple pieces of image data acquired at mutually different table top positions by imaging under the moving table method or the stepping-table method need to be synthesized into a single piece of image data, the image reconstruction unit 45 performs compound processing for connecting pieces of image data generated by image reconstruction processing, based on the positional information of the table top obtained from the table control unit 49.

Furthermore, when the echo data is acquired by PI using multiple coil elements 24c, a piece of image data corresponding to each coil element 24c is generated. Since a fold is occurred in each piece of image data, the image reconstruction unit 45 performs unfolding processing, which is post-processing in PI, based on conditions for PI such as the number of the coil elements 24c (the speed scale). This generates a single unfolded piece of image data from the multiple pieces of image data each having a fold. Sensitivity distribution of each coil element 24c is used for unfolding processing.

The generated image data and the connected image data are written and stored in the real space database 47 by the image reconstruction unit 45.

Then in step S5, the blood flow image generating unit 48 obtains the image data stored in the real space database 47 and generates blood flow image data according to the instruction of an image processing way from the interface unit 41. In other words, when the instruction of the automatic subtraction processing is received from the interface unit 41, the blood flow image generating unit 48 generates an MRA image with arteriovenous separation by subtraction processing between pieces of image data acquired in a diastole and a systole of a cardiac cycle by an FS-FBI sequence. When the instruction of the automatic MIP processing is received from the interface unit 41, the blood flow image generating unit 48 generates a projection image for displaying as an MRA image by performing MIP processing to the three-dimensional image data obtained from the real space database 47. Then, the blood flow image generating unit 48 displays the generated MRA image on the display unit 34.

Consequently, the display unit 34 displays the blood flow image at each imaging portion. Therefore, a user can use the blood flow image of the whole body of the object P for diagnosis without newly setting an imaging condition.

Even if imaging is performed according to set imaging conditions and images are being displayed, each of an imaging condition, an imaging order and an image processing way can be changed. This means imaging can be interrupted or a plan of imaging conditions to multiple imaging portions can be changed even during imaging. For example, a plan to use another imaging condition can be incorporated during imaging by an FBI sequence as whole body imaging, and a plan consisting of another imaging condition can be inserted after whole body imaging or portion imaging. If an imaging condition can be changed during imaging in this way, the remaining needless imaging can be canceled when a lesion location is detected and an imaging condition to acquire more detailed data focused on a lesion location can be set.

As described above, the magnetic resonance imaging apparatus 20 can collectively select imaging conditions for various imaging such as an MRA to meet each purpose with regard to respective imaging portions and can set imaging conditions over multiple imaging portions before data acquisition by linking the imaging conditions with the imaging portions respectively. Therefore, according to the magnetic resonance imaging apparatus 20, imaging such as non-contrast-enhanced MRA throughout a whole body can be performed with simple operation. This means pieces of data can be acquired from multiple imaging portions automatically without resetting an imaging condition, a coil position and a position of an object P for each imaging section.

Note that, in the magnetic resonance imaging apparatus 20, a PPG (peripheral pulse gating) signal can be used as a synchronization signal instead of an ECG signal. The PPG signal, for example, is obtained by detecting a pulse wave of a fingertip as an optical signal. When using a PPG signal as a synchronization signal, a PPG signal detection unit is provided.

What is claimed is:

1. A magnetic resonance imaging (MRI) apparatus comprising:
    MRI system components including static and gradient magnetic field generators, at least one radio frequency (RF) coil coupled to an imaging area within magnetic fields generated by the static and gradient magnetic field generators, an RF transmitter, an RF receiver, a display and a computer control system connected to control other MRI system components, said control computer system having at least one computer processor and memory being configured to
    concurrently display (a) an identity of plural different imaging regions of a subject and (b) plural MR imaging conditions for each of plural identified different imaging regions, the plural MR imaging conditions including at least one operator-selectable type of an MR imaging pulse sequence for non-contrast-enhanced imaging, or at least one operator-selectable parameter of the MR imaging pulse sequence, and wherein the plural identified different imaging regions for identified different anatomical regions correspond to plural different positions of a table used to transport the subject from one imaging position to another;
    select, via operator input, plural different imaging regions from among displayed plural regions and select or set respective imaging conditions corresponding to each of selected plural different imaging regions;
    set, via the display and operator input, a temporal order of imaging order for each of the selected plural imaging regions;
    acquire plural MR data sets respectively corresponding to the selected plural different imaging regions using selected or set respective MR imaging conditions, wherein the plural MR data sets are acquired automatically and sequentially in accordance with the set temporal order of imaging for each of the selected plural imaging regions; and
    generate image data based on the plural MR data sets respectively corresponding to the selected plural different imaging regions.

2. A magnetic resonance imaging apparatus according to claim 1, wherein respective data sets are acquired sequentially from the selected plural imaging regions.

3. A magnetic resonance imaging apparatus according to claim 1, said control system being further configured to perform image processing to the image data, and
    wherein an acquisition sequence for respective data sets is set by an operation of an operator input device.

4. A magnetic resonance imaging apparatus according to claim 1, wherein at least one of the plural different imaging regions and an acquisition sequence order to acquire respective data sets from the plural different imaging regions is set using a correspondingly configured coil array.

5. A magnetic resonance imaging apparatus according to claim 1, wherein an imaging condition is set for non-contrast-enhanced MRA.

6. A magnetic resonance imaging apparatus according to claim 1,
    wherein a non-contrast-enhanced MRA sequence for acquiring an MRA image by subtracting between data sets generated based on respective magnetic resonance signals acquired at systole and diastole of a cardiac cycle is made selectable to be selected as one of respective imaging conditions and an intensity of a spoiler pulse of the non-contrast-enhanced MRA sequence is made selectable to be set.

7. A magnetic resonance imaging apparatus according to claim 1, wherein a table top is moved for repositioning an object each time data acquisition from one imaging region is completed.

8. A magnetic resonance imaging apparatus according to claim 1, wherein said control system is further configured to:
    generate MRA image data in which an artery and a vein are separated by performing subtraction processing to respective image data sets corresponding to systole and diastole of a cardiac cycle; and
    give instruction information to perform the subtraction processing automatically subsequent to data acquisition for generating the respective image data sets corresponding to systole and diastole.

9. A magnetic resonance imaging apparatus according to claim 1, wherein said control system is further configured to:
    generate MRA image data by performing weighted subtraction processing to the image data; and
    give instruction information to perform the weighted subtraction processing automatically.

10. A magnetic resonance imaging apparatus according to claim 1, wherein said control system is further configured to:
    perform projection processing on generated three-dimensional image data; and
    give instruction information to perform the projection processing automatically subsequent to data acquisition for generating the three-dimensional image data.

11. A magnetic resonance imaging apparatus according to claim 1, wherein said control system is further configured to:
    to perform post-processing to the image data; and
    give instruction information to perform the post-processing automatically.

12. A magnetic resonance imaging apparatus according to claim 1, wherein respective data sets are acquired with a phased array coil which configures coil elements to acquire respective plural MR data sets from the plural different imaging regions.

13. A magnetic resonance imaging apparatus according to claim 1,
wherein respective data sets are acquired from the plural different aging regions with a whole body coil.

14. A magnetic resonance imaging apparatus according to claim 1, wherein a number of coil elements is set as an imaging condition for parallel imaging by which respective data sets are acquired while skipping at least one phase encode by using the coil elements.

15. A magnetic resonance (MR) imaging method comprising:
concurrently displaying (a) an identity of plural different imaging regions of a subject and (b) plural MR imaging conditions for each of plural identified different imaging regions, the plural MR imaging conditions including at least one operator-selectable type of an MR imaging pulse sequence for non-contrast-enhanced MR imaging, or at least one operator-selectable parameter of the MR imaging pulse sequence, and wherein the plural identified different imaging regions for identified different anatomical regions correspond to plural different positions of a table used to transport the subject from one imaging position to another;
selecting via operator input plural different imaging regions among displayed plural different imaging regions and selecting or setting respective MR imaging conditions corresponding to each of selected plural different imaging regions;
setting, via an operator display and input, a temporal order of imaging for each of the selected plural imaging regions set by the operator for each of the selected plural imaging regions;
acquiring plural data sets respectively corresponding to the selected plural different imaging regions according to selected or set respective MR imaging conditions, wherein the plural MR data sets are acquired automatically and sequentially in accordance with the temporal order of imaging; and
generating MR image data based on MR data sets respectively corresponding to the selected plural different imaging regions.

* * * * *